United States Patent
Uyama et al.

(10) Patent No.: US 12,090,218 B2
(45) Date of Patent: Sep. 17, 2024

(54) WATER-IN-OIL EMULSION COMPOSITION

(71) Applicant: Shiseido Company, Ltd., Tokyo (JP)

(72) Inventors: Makoto Uyama, Tokyo (JP); Takumi Watanabe, Tokyo (JP); Ayano Matsuo, Tokyo (JP)

(73) Assignee: Shiseido Company, Ltd., Tokyo (JP)

( * ) Notice: Subject to any disclaimer, the term of this patent is extended or adjusted under 35 U.S.C. 154(b) by 504 days.

(21) Appl. No.: 17/618,664

(22) PCT Filed: Feb. 28, 2020

(86) PCT No.: PCT/JP2020/008513
§ 371 (c)(1),
(2) Date: Dec. 13, 2021

(87) PCT Pub. No.: WO2020/250503
PCT Pub. Date: Dec. 17, 2020

(65) Prior Publication Data
US 2022/0370308 A1    Nov. 24, 2022

(30) Foreign Application Priority Data
Jun. 14, 2019   (JP) .................................. 2019-111179

(51) Int. Cl.
*A61K 8/06*       (2006.01)
*A61K 8/81*       (2006.01)
*A61K 8/92*       (2006.01)

(52) U.S. Cl.
CPC ............ *A61K 8/064* (2013.01); *A61K 8/8147* (2013.01); *A61K 8/92* (2013.01); *A61K 2800/805* (2013.01)

(58) Field of Classification Search
CPC ............ A61K 7/00; A61K 7/42; C08F 220/26
USPC ......................................................... 424/401
IPC ......................... A61Q 19/00; A61K 7/00,7/42
See application file for complete search history.

(56) References Cited

U.S. PATENT DOCUMENTS

| | | | |
|---|---|---|---|
| 6,410,605 B1 * | 6/2002 | Shimada | A61K 8/044 523/210 |
| 2008/0199420 A1 * | 8/2008 | Wendel | A61Q 19/00 424/78.02 |
| 2017/0348219 A1 | 12/2017 | Uyama et al. | |

FOREIGN PATENT DOCUMENTS

| | | | |
|---|---|---|---|
| JP | 2005350366 A | * | 12/2005 |
| JP | 2009-242294 A | | 10/2009 |
| JP | 2010-037230 A | | 2/2010 |
| WO | WO-2016/098456 A1 | | 6/2016 |

* cited by examiner

*Primary Examiner* — Walter E Webb
(74) *Attorney, Agent, or Firm* — Foley & Lardner LLP

(57) ABSTRACT

To provide a water-in-oil emulsified composition which highly encapsulates a water content, has high viscosity, and is excellent in emulsification stability.
The water-in-oil emulsified composition of the present disclosure comprises a dispersion medium comprising an oil content, and an oil-soluble copolymer having a monomer unit obtained from a specific hydrophilic monomer, and a monomer unit obtained from a specific hydrophobic monomer; and water droplets dispersed in the dispersion medium, wherein the oil content contains 60% by mass or more of polar oil with an IOB of 0.10 or more, and wherein the water droplets contain water and a surfactant, and the content of the water is 30% by mass or more based on the total amount of the composition.

7 Claims, 1 Drawing Sheet

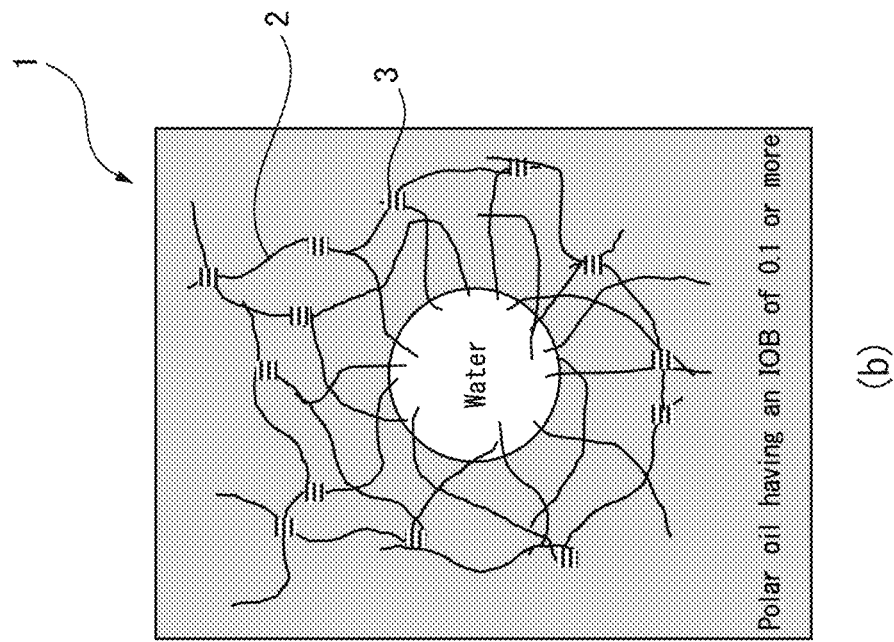
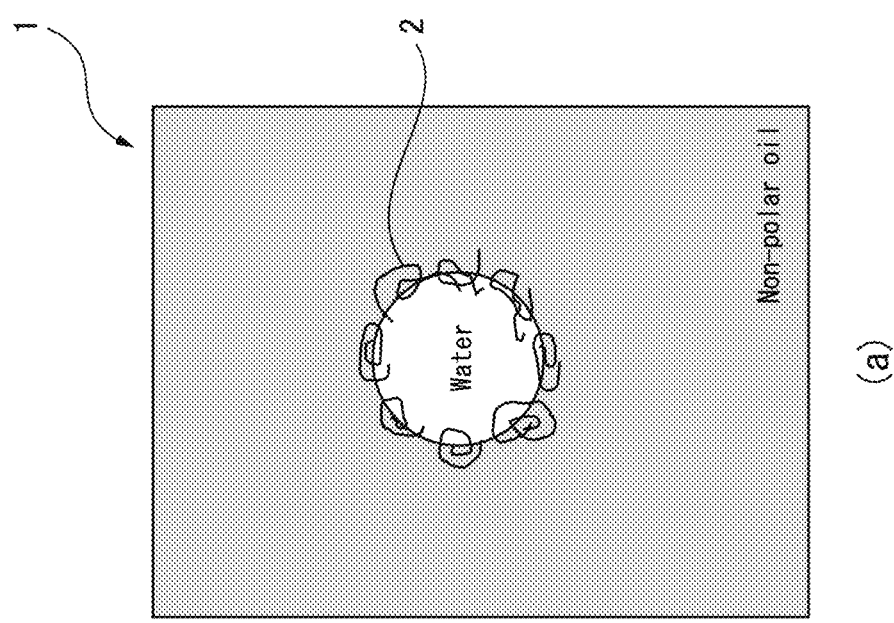

WATER-IN-OIL EMULSION COMPOSITION

CROSS-REFERENCE TO RELATED APPLICATIONS

This application is the U.S. National Stage of PCT/JP2020/008513, filed Feb. 28, 2020, which claims priority to JP 2019-111179, filed Jun. 14, 2019.

FIELD

The present disclosure relates to a water-in-oil emulsified composition.

BACKGROUND

For example, in the field of cosmetics, a water-in-oil emulsified composition capable of imparting not only an oil content and an oil-soluble ingredient but also moisture and a water-soluble ingredient to the skin is used. Then, in order to improve the usability and the like of cosmetics, attempts have been made to thicken or gel in a water-in-oil emulsified composition.

PTL 1 discloses a high internal aqueous phase water-in-oil type emulsion cosmetic containing (A) a polyglycerin-modified silicone, (B) a partially crosslinked organopolysiloxane polymer containing a long-chain alkyl group, (C) a volatile silicone oil, and (D) water, and containing 70% by mass or more of an aqueous phase component containing component (D).

PTL 2 discloses a water-in-oil emulsified composition comprising an oil phase and an aqueous phase, wherein the oil phase contains an organic modified clay mineral, (a) a fatty acid or a hydroxy fatty acid having 8 to 30 carbon atoms, (b) a dibasic acid having 12 to 36 carbon atoms, and (c) an ester compound obtained from a glycerin, or a glycerin condensation product, a silicone polymer having a three dimensional crosslinked structure, and a silicone oil.

PTL 3 discloses a water-in-oil type emulsified cosmetic comprising an oily gelling agent consisting of a copolymer obtained from a specific hydrophobic monomer and a specific hydrophilic monomer.

CITATION LIST

Patent Literature

[PTL 1] Japanese Unexamined Patent Publication (Kokai) No. 2009-242294
[PTL 2] Japanese Unexamined Patent Publication (Kokai) No. 2010-037230
[PTL 3] WO 2016/098456

SUMMARY

Technical Problem

As also described in PTL 2, it is generally difficult to thicken the oil content. In particular, in the case of a water-in-oil type emulsified composition containing a large amount of water, it has been more difficult to thicken such a composition and to emulsify and stabilize it together with it because the thickening mechanism of the thickener in which the oil and water coexist and are blended becomes complicated.

Accordingly, it is a subject of the present disclosure to provide a water-in-oil emulsified composition which highly encapsulates a water content, has high viscosity, and is excellent in emulsification stability.

Solution to Problem

Embodiment 1

A water-in-oil emulsified composition comprising,
a dispersion medium comprising an oil content, and an oil-soluble copolymer having a monomer unit obtained from at least one hydrophilic monomer selected from Formula 1 and Formula 2 below, and a monomer unit obtained from a hydrophobic monomer of Formula 4 below; and
water droplets dispersed in the dispersion medium,
wherein the oil content contains 60% by mass or more of polar oil with an IOB of 0.10 or more, and
wherein the water droplets contain water and a surfactant, and the content of the water is 30% by mass or more based on the total amount of the composition:

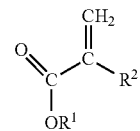

Formula 1 wherein,
$R^1$ is a hydrogen atom, a glyceryl group, a linear or branched hydroxyalkyl group having 1 to 4 carbon atoms, or a polypropylene glycol group indicated by $-(C_3H_6O)_nH$ and where n is an integer of 2 to 10, and
$R^2$ is a hydrogen atom or a methyl group,

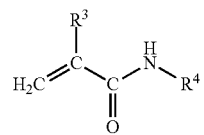

Formula 2 wherein,
$R^3$ is a hydrogen-atom or a methyl-group, and
$R^4$ is a linear or branched alkyl or hydroxyalkyl group having 1 to 4 carbon atoms, or a substituent of Formula 3 below.

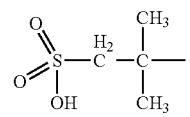

Formula 3

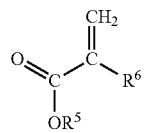

Formula 4 wherein,
$R^5$ is a linear or branched alkyl group having 16 to 22 carbon atoms, and
$R^6$ is a hydrogen atom or a methyl group.

Embodiment 2

The composition of embodiment 1, wherein the monomer of formula 1 is selected from at least one of 2-hydroxyethyl (meth)acrylate, glyceryl (meth)acrylate, PPG-6 (meth)acrylate, 2-hydroxypropyl (meth)acrylate, 2-hydroxy-2-methylpropyl (meth)acrylate, and (meth)acrylic acid, and wherein the monomer of formula 2 is selected from at least one of N-(2-hydroxyethyl) (meth)acrylamide, N-isopropyl (meth)acrylamide, and 2-(meth)acrylamide-2-methylpropanesulfonic acid.

Embodiment 3

The composition according to embodiment 1 or 2, wherein the monomer of Formula 4 is selected from at least one of cetyl (meth)acrylate, stearyl (meth)acrylate, isostearyl (meth)acrylate, and behenyl (meth)acrylate.

Embodiment 4

A composition according to any of embodiments 1 to 3, wherein in the oil-soluble copolymer, a monomer unit of the hydrophilic monomer is contained in a range of 30 to 50 mol %, and a monomer unit of the hydrophobic monomer is contained in a range of 50 to 70 mol %.

Embodiment 5

A composition according to any of embodiments 1 to 4, wherein the water droplet has an average particle size of 10 μm or less.

Embodiment 6

A composition according to any of embodiments 1 to 5, further comprising a clay mineral.

Embodiment 7

A cosmetic base material comprising a composition according to any of embodiments 1 to 6.

Advantageous Effects of Invention

According to the present disclosure, it is possible to provide a water-in-oil emulsified composition which highly encapsulates a water content, has high viscosity, and is excellent in emulsification stability.

BRIEF DESCRIPTION OF DRAWINGS

FIG. 1 (a) is a schematic diagram of a water-in-oil emulsified composition when a non-polar oil is used as a continuous phase, and FIG. 1 (b) is a schematic diagram of a water-in-oil emulsified composition when a polar oil having an IOB of 0.1 or more is used as a continuous phase.

DESCRIPTION OF EMBODIMENTS

Hereinafter, embodiments of the present disclosure will be described in detail. The present disclosure is not limited to the following embodiments, and may be variously modified and practiced within the scope of the present invention.

A water-in-oil emulsified composition of the present disclosure (sometimes simply referred to as an "emulsified composition") comprises an oil content, and a dispersion medium comprising an oil-soluble copolymer having a monomer unit obtained from at least one hydrophilic monomer selected from Formula 1 and Formula 2 described above and a monomer unit obtained from a hydrophobic monomer of Formula 4 described above, and a water droplet dispersed in the dispersion medium, wherein the oil content contains 60% by mass or more of a polar oil having an IOB of 0.10 or more, the water droplet contains water and a surfactant, and the content of water is 30% by mass or more based on the total amount of the composition.

Although not limited by the principle, it is considered that the action principle of such a water-in-oil type emulsified composition with high viscosity and excellent emulsion stability is as follows.

The oil-soluble copolymer of the present disclosure is obtained from a specific hydrophobic monomer and a specific hydrophilic monomer. It is considered that the hydrophobic monomer among them, in addition to exhibiting a function of exhibiting solubility in an oil content, is easily crystallized and crystallizes by a hydrophobic monomer unit between the copolymers as the copolymers approach each other, so that a network structure is formed in such a manner as to incorporate an oil content. Further, since the hydrophilic monomer unit between the copolymers is also bonded by hydrogen bonding, it is considered that the same network structure is formed. When such an oil-soluble copolymer is blended with respect to a composition containing no water content or containing water content in an amount as low as about 10% by mass, as shown in PTL 3, since the effect due to water content is small, the copolymer is easily dispersed in an oil content which is a continuous phase. As a result, it is considered that, since the network structure described above is easily expressed, the viscosity of the composition can be increased regardless of the type of oil content.

On the other hand, in the case of a composition with a high degree of water content (30 mass % or more), since the oil-soluble copolymer contains a hydrophilic monomer unit, it tends to be oriented near the interface of the aqueous phase. Since the oil-soluble copolymer of the present disclosure is more easily dissolved in a polar solvent such as an ester oil than a non-polar oil such as a hydrocarbon oil, the non-polar oil can be classified as a poor solvent and the polar oil as a good solvent with respect to the oil-soluble copolymer. When a non-polar oil which is a poor solvent is used as a continuous phase or when a proportion of a polar oil is small in a continuous phase which is an oil phase, it is considered that the oil-soluble copolymer is present in a shrunken state near an interface between an aqueous phase and an oil phase as shown in FIG. 1 (a). As a result, it is considered that such a copolymer hardly increases the viscosity of the composition because it is difficult to form the network structure described above.

The water-in-oil emulsified composition of the present disclosure contains, as a continuous phase, 60% by mass or more of a polar oil having an JOB of 0.10 or more which functions as a good solvent with respect to an oil-soluble copolymer. As a result, it is considered that the oil-soluble copolymer is present so that the hydrophobic monomer unit spreads as shown in FIG. 1 (b), rather than shrinking in the vicinity of the interface between the aqueous phase and the oil phase, and thus the network structure described above is easily formed, so that the viscosity of the composition can be increased. Further, in addition to increasing the viscosity of the composition, it is considered that the hydrophobic monomer unit present in a spread state becomes a steric hindrance, and the coalescence of adjacent water droplets is suppressed, so that the emulsification stability of the emulsified composition is improved.

Since the polar oil used in the present disclosure has a hydrogen bonding ability unlike a nonpolar oil, it is considered that, as shown in FIG. 1 (b), a copolymer adsorbed at an interface between an aqueous phase and an oil phase, or a copolymer dispersed in an oil phase is subjected to an effect such that a copolymer is bonded together by hydrogen bonding. It is considered that such an effect also contributes to the development of thickening property.

Definitions of terms in the present disclosure are as follows.

In the present disclosure, a "hydrophilic monomer" is intended to be a monomer which dissolves in water in an arbitrary ratio, and a "hydrophobic monomer" is intended to be a monomer other than that, that is, a monomer which is basically immiscible with water.

In the present disclosure, "(meth)acryl" means acryl or methacryl.

<<Water-In-Oil Emulsified Composition>>

The water-in-oil emulsified composition of the present disclosure is excellent in emulsification stability. Here, emulsification stability can be intended, for example, a state in which there is no separation, and preferably no change in the size of emulsified particles (water droplets) at 0° C. to 37° C. for 4 weeks, preferably at 50° C. for 4 weeks.

The water-in-oil emulsified composition of the present disclosure exhibits an excellent thickening effect by an oil-soluble copolymer described later. The thickening property of such a composition can be evaluated using a B-type viscometer (TVB-type viscometer TVB-10, manufactured by Toki Sangyo Co., Ltd.). For example, the viscosity of the water-in-oil emulsification composition of the present disclosure measured under the conditions of a rotor number H6, 30° C., and 10 revolutions per minute can achieve 3,000 mPa·s or more, 5,000 mPa·s or more, 7,000 mPa·s or more, 9,000 mPa·s or more, 10,000 mPa·s or more, or 13,000 mPa·s or more, and can achieve 70,000 mPa·s or less, 65,000 mPa·s or less, 55,000 mPa·s or less, or 50,000 mPa·s or less.

<Oil-Soluble Copolymer>

The water-in-oil emulsified composition of the present disclosure comprises an oil-soluble copolymer in a dispersion medium. Such an oil-soluble copolymer has a monomer unit obtained from at least one hydrophilic monomer selected from Formula 1 and Formula 2 described above, and a monomer unit obtained from a hydrophobic monomer of Formula 4 described above. Each monomer unit of the above may be composed of a single monomer unit or may be composed of two or more monomer units. For example, a hydrophilic monomer unit may be composed of a single monomer unit, and a hydrophobic monomer unit may be composed of two kinds of monomer units.

There is no particular limitation on the polymer form of the oil-soluble copolymer, and for example, a random type, a block type, or the like can be employed, but from the viewpoint of ease of synthesis, it is preferable to be a random type.

Although the proportion of monomer units obtained from the above hydrophilic monomers to those obtained from the above hydrophobic monomers in the oil-soluble copolymer is not specifically limited, for example, from the viewpoint of thickening, emulsification stability, etc., monomer units of hydrophilic monomers may contain 30 mol % or more, 32 mol % or more, 35 mol % or more, or 40 mol % or more, and 50 mol % or less, 48 mol % or less, or 45 mol % or less.

From the viewpoint of thickening, emulsification stability, solubility in oil, etc., monomeric units of hydrophobic monomers may contain 50 mol % or more, 52 mol % or more, or 55 mol % or more, and 70 mol % or less, 68 mol % or less, 65 mol % or less, or 60 mol % or less.

The content of the oil-soluble copolymer may be 0.3% by mass or more, 0.4% by mass or more, or 0.5% by mass or more, and may be 3.0% by mass or less, 2.5% by mass or less, or 2.0% by mass or less, based on the total amount of the emulsified composition.

The proportion of the oil-soluble copolymer to the total amount of the oil content may be 1.0% by mass or more, 1.2% by mass or more, or 1.5% by mass or more, and may be 5.0% by mass or less, 4.5% by mass or less, or 4.0% by mass or less. Since the water-in-oil emulsified composition of the present disclosure also exhibits a thickening effect due to hydrogen bonding based on the polar oil described above and a thickening effect based on a packing action of water droplets described later, it is possible to exhibit an excellent thickening property even when the oil-soluble copolymer is in such a relatively low amount.

(Hydrophilic Monomer)

As the hydrophilic monomer, at least one monomer selected from the following Formula 1 and Formula 2 can be used.

a. Monomer of Formula 1

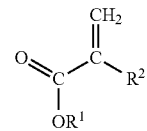

Formula 1

In Formula 1, $R^1$ is a hydrogen atom, a glyceryl group, a linear or branched hydroxyalkyl group having 1 to 4 carbon atoms, or polypropylene glycol group indicated by —$(C_3H_6O)_n$H and where n is an integer of 2 to 10, and $R^2$ is a hydrogen atom or a methyl group. Examples of the hydroxyalkyl group include 2-hydroxyethyl group, 2-hydroxypropyl group, 2-hydroxyethyl-2-methylpropyl group, 2-hydroxybutyl group, 3-hydroxybutyl group, and 4-hydroxybutyl group.

Specific examples of the hydrophilic monomer represented by Formula 1 include 2-hydroxyethyl (meth)acrylate, glyceryl (meth)acrylate, PPG-6 (meth)acrylate, 2-hydroxypropyl (meth)acrylate, 2-hydroxy-2-methylpropyl (meth)acrylate, and (meth)acrylic acid. Among them, from the viewpoint of thickening, emulsification stability, and the like, glyceryl (meth)acrylate is preferred, and glyceryl methacrylate is more preferred.

b. Monomer of Formula 2

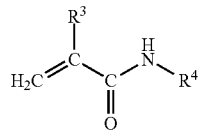

Formula 2

In Formula 2, $R^3$ is a hydrogen atom or a methyl group, and $R^4$ is a linear or branched alkyl or hydroxyalkyl group having 1 to 4 carbon atoms, or a substituent of Formula 3 below.

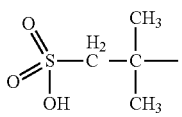

Formula 3

Here, the alkyl group in $R^4$ may include, for example, ethyl group, propyl group, isopropyl group, and butyl group, and the hydroxyalkyl group may include, for example, 2-hydroxyethyl group, 2-hydroxypropyl group, 2-hydroxyethyl-2-methylpropyl group, 2-hydroxybutyl group, 3-hydroxybutyl group, and a 4-hydroxybutyl group.

Specific examples of the hydrophilic monomer represented by Formula 2 include N-(2-hydroxylethyl) (meth)acrylamide, N-isopropyl (meth)acrylamide, and 2-(meth)acrylamide-2-methylpropanesulfonic acid. Among them, from the viewpoint of thickening, emulsification stability, and the like, N-(2-hydroxyethyl) (meth)acrylamide is preferred, and N-(2-hydroxylethyl) acrylamide is more preferred.

(Hydrophobic Monomer)
c. Monomer of Formula 4

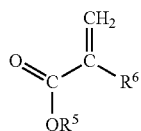

Formula 4

In Formula 4, $R^5$ is a linear or branched alkyl group having 16 to 22 carbon atoms, and $R^6$ is a hydrogen atom or a methyl group. Here, examples of the linear or branched alkyl group having 16 to 22 carbon atoms include a cetyl group, a stearyl group, an isostearyl group, and a behenyl group. Among them, from the viewpoint of thickening, emulsification stability, compatibility with an oil content, and the like, a linear alkyl group having 16 to 22 carbon atoms is preferred, and a cetyl group, a stearyl group, and a behenyl group are more preferred.

Such a hydrophobic monomer is a (meth)acrylic acid alkyl ester, i.e., an ester consisting of a (meth)acrylic acid and an alcohol having a linear or branched alkyl group of 16 to 22 carbon atoms. Specific examples include a cetyl (meth)acrylate, a stearyl (meth)acrylate, an isostearyl (meth)acrylate, and a behenyl (meth)acrylate. Among them, from the viewpoint of thickening, emulsification stability, compatibility with an oil content, and the like, a cetyl (meth)acrylate, a stearyl (meth)acrylate, and a behenyl (meth)acrylate are preferred, and a stearyl (meth)acrylate is more preferred.

(Optional Monomer)
From the viewpoint of thickening and emulsification stability, the oil-soluble copolymer of the present disclosure preferably does not contain a monomer unit obtained from a monomer other than the above Formula 1, Formula 2, and Formula 4, but may further have such a monomer unit as long as the effect of the present invention is not impaired. The ratio of such a monomer unit may be in the range of 30 mol % or less, 20 mol % or less, 10 mol % or less, or 5 mol % or less, based on the total amount of the monomer unit constituting.

Examples of the monomer other than Formula 1, Formula 2, and Formula 4 described above include one or more kinds of monomers selected from the group consisting of various anionic monomers, cationic monomers, nonionic monomers, and monomers other than these.

Specific examples of the hydrophilic monomer other than the hydrophilic monomer represented by Formula 1 or Formula 2 include vinylpyrrolidone, vinylimidazole, methoxypolyethylene glycol (metha)acrylate, N,N-dimethyl (meth)acrylamide, N,N-diethyl (meth)acrylamide, acryloylmorpholine, methacryloylmorpholine, N-(2-methacryloyloxyethyl)ethyleneurea, and 2-methacryloyloxyethylphosphorylcholine.

Further, examples of the hydrophobic monomer other than the hydrophobic monomer represented by Formula 4 include methylstyrene, styrene, benzyl (meth)acrylate, phenyl (meth)acrylate, tris (trimethylsiloxy) silylpropyl (meth)acrylate, and (meth)acrylic acid-2-perfluorohexyl-2-ethyl.

(Method for Producing an Oil-Soluble Copolymer)
The oil-soluble copolymer of the present disclosure can be obtained by a known polymerization method. Although not limited to the following method, for example, a mixture of a hydrophilic monomer and a hydrophobic monomer, a polymerization solvent, and a polymerization initiator are charged into a reaction vessel and maintained for several hours while being warmed so as to maintain a constant temperature to proceed the polymerization reaction. Then, by distilling off the polymerization solvent from the solution in the reaction vessel, an oil-soluble copolymer can be obtained.

Further, a copolymer can be obtained by a living radical polymerization method. In this case, it is possible to easily adjust the molecular weight of the copolymer and to produce a copolymer having a narrow molecular weight distribution.

d. Polymerization Solvent
As the polymerization solvent, a solvent which does not exhibit reactivity with respect to the functional group of the monomer is appropriately selected. Polymerization solvents include, but are not limited to, the following: hydrocarbonic solvents such as n-hexane, n-octane, n-decane, isodecane, cyclohexane, methylcyclohexane, toluene, xylene, ethylbenzene, cumene; alcoholic solvents such as methanol, ethanol, n-propanol, isopropanol, n-butanol, isobutanol, n-hexanol, benzyl alcohol, cyclohexanol; hydroxyl-containing glycol ethers such as ethylene glycol, diethylene glycol, propylene glycol, dipropylene glycol, methylcellosolb, ethylcerosolb, butylcerosolb, propylene glycol monomethyl ether, propylene glycol monoethyl ether, propylene glycol propyl ether, butylcarbitol, butyltriethylene glycol, methyldipropylene glycol; glycolic solvents such as diglyme, triglyme, methyl cellosolve acetate, propylene glycol monomethyl ether acetate, dipropylene glycol butyl ether acetate, diethylene glycol monobutyl ether acetate; ethereal solvents such as diethyl ether, dipropyl ether, methylcyclopropyl ether, tetrahydrofuran, dioxane, anisole; ketone solvents such as dimethyl ketone, diethyl ketone, ethyl methyl ketone, isobutyl methyl ketone, cyclohexanone, isophorone, acetophenone; ester solvents such as methyl acetate, ethyl acetate, butyl acetate, propyl acetate, methyl butyrate, ethyl butyrate, caprolactone, methyl lactate, ethyl lactate; halogenated solvents such as chloroform, dichloromethane, dichloroethane, o-dichlorobenzene; amide solvents such as formamide, N,N-dimethylformamide, N,N-dimethylacetamide, 2-pyrrolidone, N-methyl-2-pyrrolidone, ε-caprolactam; dimethyl sulfoxide, sulfolane, tetramethylurea, ethylene carbonate, propylene carbonate, dimethyl carbonate, diethyl carbonate, nitromethane, acetonitrile, nitrobenzene, dioctylphthalate, and the like.

e. Polymerization Initiator

As the polymerization initiator, conventionally known ones can be used, and there is no particular limitation, and for example, an organic peroxide or an azo compound or the like can be used. Specific examples thereof include benzoyl peroxide, dicumylperoxide, diisopropyl peroxide, di-t-butyl peroxide, t-butyl peroxybenzoate, t-hexyl peroxy benzoate, t-butyl peroxy-2-ethyl hexanoate, t-hexyl peroxy-2-ethylhexanoate, 1,1-bis(t-butylperoxy)3,3,5-trimethylcyclohexane, 2,5-dimethyl-2,5-bis(t-butylperoxy)hexyl-3,3-isopropylhydroperoxide, t-butyl hydroperoxide, dicumyl hydroperoxide, acetyl peroxide, bis(4-t-butylcyclohexyl) peroxydicarbonate, isobutyl peroxide, 3,3,5-trimethylhexanoyl peroxide, lauryl peroxide, 1,1-bis(t-butyl peroxy) 3,3,5-trimethylcyclohexane, 1,1-bis(t-hexylperoxy)3,3,5-trimethylcyclohexane, 2,2'-azobis(isobutyronitrile), 2,2'-azobis(2,4-dimethylvaleronitrile), 2,2'-azobis(4-methoxy-2,4-dimethylvaleronitrile), dimethyl 2,2'-azobis(isobutyrate).

f. Polymerization Time

The time for maintaining the reflux state, that is, the polymerization time, is preferably continued until there is no monomer, and is not particularly limited, and may be, for example, 1 hours or more, 2 hours or more, or 3 hours or more, and may be 144 hours or less, 72 hours or less, or 48 hours or less.

g. Polymerization Atmosphere

The polymerization atmosphere is not particularly limited and may be polymerized as it is under an atmospheric atmosphere, that is, oxygen may be present within a normal range in the polymerization system, or may be carried out under an atmosphere of an inert gas such as nitrogen or argon to remove oxygen if necessary. Impurities in the various materials to be used may be removed by distillation, activated carbon, or alumina, but commercial products may be used as is. Also, the polymerization may be carried out under light shielding and may be carried out in a transparent container such as glass.

h. Other Ingredients that Contribute to the Polymerization Reaction

For example, other ingredients such as a chain transfer agent may be added to the reaction vessel if necessary for adjusting the molecular weight of the copolymer or the like. Such a chain transfer agent is not particularly limited, and examples thereof include a compound having a mercapto group such as lauryl mercaptan, thioglycerol, and the like; an inorganic salt such as sodium hypophosphite, sodium bisulfite, and the like; and a α-methylstyrene dimer. The amount of the chain transfer agent to be used is appropriately determined so that the molecular weight of the copolymer is in the range of interest, but is usually preferably in the range of 0.01 to 10% by mass based on the monomer.

<Oil Content>

The water-in-oil emulsified composition of the present disclosure contains an oil content as a dispersion medium. The content of the oil content may be 20% by mass or more, 25% by mass or more, or 30% by mass or more, and may be 70% by mass or less, 65% by mass or less, or 60% by mass or less, based on the total amount of the emulsified composition.

As the oil content, a polar oil having an IOB of 0.10 or more may be contained in a proportion of 60% by mass or more, 65% by mass or more, 70% by mass or more, or 75% by mass or more based on the entire oil content. There is no particular limitation on the upper limit value of the proportion of such a polar oil, and may be, for example, 100% by mass or less.

The IOB value of the polar oil may be, for example, 0.11 or more, 0.12 or more, or 0.13 or more, and may be 0.50 or less, 0.45 or less, or 0.40 or less. Here, the IOB value is an abbreviation of Inorganic/Organic Balance (inorganic/organic ratio), and is a value representing a ratio of an inorganic value to an organic value, and is an indicator indicating a degree of polarity of an organic compound. The IOB value is specifically expressed as the IOB value=inorganic value/organic value. For each of the "inorganic value" and the "organic value", an "inorganic value" and an "organic value" corresponding to various atoms or functional groups are set (for example, an "organic value" is 20 for one carbon atom in a molecule and an "inorganic value" is 100 for one hydroxyl group), and the IOB value of the organic compound can be calculated by integrating the "inorganic value" and the "organic value" of all atoms and functional groups in an organic compound (see, for example, written by Yoshio Koda, "Organic Conceptual Chart—Basics and Applications-", p. 11 to 17, Sankyo Publishing, 1984).

Examples of polar oils satisfying such conditions include oleic acid (IOB value=0.42), isostearic acid (IOB value=0.43), isopropyl myristate (IOB value=0.18), octyl palmitate (IOB value=0.13), isopropyl palmitate (IOB value=0.16), butyl stearate (IOB value=0.14), hexyl laurate (IOB value=0.17), myristyl myristate (IOB value=0.11), decyl oleate (IOB value=0.11), isononyl isonononanoate (IOB value=0.20), isotridecyl isonononanoate (IOB value=0.15), cetyl ethylhexanoate (IOB value=0.13), pentaerythrityl tetraethylhexanoate (IOB value=0.35), diethylhexyl succinate (IOB value=0.32), glycol distearate (IOB value=0.16), glyceryl diisostearate (IOB value=0.29), neopentyl glycol dicaprate (IOB value=0.25), diisostearyl malate (IOB value=0.28), trimethylolpropane triisostearate (IOB value=0.16), glyceryl tri2-ethylhexanoate (triethylhexanoin) (IOB value=0.35), trimethylolpropane trioctanoate (IOB value=0.33), trimethylolpropane triisostearate (IOB value=0.16), diisobutyl adipate (IOB value=0.46), N-lauroyl-L-glutamic acid-2-octyldodecyl ester (IOB value=0.29), 2-hexyldecyl adipate (IOB value=0.16), diisopropyl sebacate (IOB value=0.40), ethylhexyl methoxycinnamate (IOB value=0.28), olive oil (IOB value=0.16), castor oil (IOB value=0.43), decyltetradecanol (IOB value=0.21), octyldodecanol (IOB value=0.26), oleyl alcohol (IOB value=0.28), 2-ethylhexyl palmitate (IOB value=0.13), 2-ethylhexyl ethylhexanoate (IOB value=0.2), triisostearin (IOB value=0.16), PPG-3 dipivalate (IOB value=0.52), tri (caprylic/capric) glyceryl (IOB value=0.33), and the like. These may be used alone or in combination of two or more thereof.

An oil content other than a polar oil having an IOB of 0.10 or more may be blended within a range not affecting the effect of the present invention. Such an oil content may be blended in a ratio of 40% by mass or less, 35% by mass or less, 30% by mass or less, 20% by mass or less, or 10% by mass or less, based on the whole oil content. Examples of such an oil content include a hydrocarbon oil, a silicone oil, a higher alcohol, and an oil-soluble polyhydric alcohol. These may be used alone or in combination of two or more thereof.

Examples of the hydrocarbon oil include liquid paraffin, tetraisobutane, hydrogenated polydecene, olefin oligomer, isododecane, isohexadecane, squalane, and hydrogenated polyisobutene.

Examples of the silicone oil include dimethylpolysiloxane (dimethicone); methylhydrogenpolysiloxane; methylphenyl silicone such as trimethylpentaphenyltrisiloxane, diphenyldimethicone, diphenylsiloxyphenyltrimethicone, phenyltrimethicone, phenyldimethicone, and the like; perfluorooctylethyl/diphenyldimethicone, and the like.

Examples of the higher alcohol include isostearyl alcohol and oleyl alcohol.

Examples of the oil-soluble polyhydric alcohol include polybutylene glycol and the like.

<Water Droplets>

The water-in-oil emulsion composition of the present disclosure comprises water droplets as an aqueous or dispersed phase, such water droplets comprising water and a surfactant. The content of water may be 30% by mass or more, 35% by mass or more, or 40% by mass or more, and may be 70% by mass or less, 65% by mass or less, or 60% by mass or less, based on the total amount of the emulsified composition.

The water droplets (emulsified particles) in the emulsified composition may have an average particle size of, for example, 10 μm or less, 9 μm or less, or 8 μm or less. The lower limit value of the average particle size is not particularly limited, but may be, for example, 0.5 μm or more or 1 μm or more. Here, the average particle size of the water droplets can be defined as an average value of the projected area circle equivalent diameters of 10 or more, preferably 100 or more, water droplets observed by an optical microscope.

Since the oil-soluble copolymer of the present disclosure is oriented around the water droplet and also exhibits a function such as an emulsification aid as in FIG. 1 (b), the particle diameter of the water droplet can be reduced in this manner. Then, an emulsified composition highly containing water droplets of such a minute size can contribute to an increase in viscosity of an emulsified composition because water droplets become densely packed.

(Water)

The water which can be used in the water-in-oil emulsified composition of the present disclosure is not particularly limited, but water used in cosmetics, quasi-drugs, and the like can be used. For example, ion-exchanged water, distilled water, ultrapure water, tap water, or the like can be used.

(Surfactant)

Surfactants (emulsifiers) are generally predominantly present near the interface between the aqueous phase and the oil phase, that is, near the outer periphery of the water droplet, and some are dispersed in the oil content. The surfactant which can be used in the water-in-oil emulsified composition of the present disclosure is not particularly limited, and known surfactants may be used alone or in combination of two or more thereof. Examples of such a surfactant include a silicone-based surfactant and a hydrocarbon-based surfactant.

As hydrocarbon-based surfactant, for example, glyceryl diisostearate, PEG-4 sorbitan triisostearate, POE(2) stearyl ether, self-emulsifying propylene glycol monostearate, glyceryl myristate, glyceryl monostearate, self-emulsifying glyceryl monostearate, glyceryl monoisostearate, glyceryl monooleate, hexaglyceryl tristearate, decaglyceryl pentastearate, decaglyceryl pentaisostearate, decaglyceryl pentaoleate, sorbitan monostearate, sorbitan tristearate, POE(6) sorbit hexastearate, POE(3) castor oil, PEG(2) monostearate, ethylene glycol monostearate, etc. can be used.

As the silicone-based surfactant, for example, a silicone-based surfactant modified by a polyether group or a polyglycerin group can be used.

Examples of the silicone-based surfactant modified by a polyether group include PEG-11 methyl ether dimethicone, PEG-10 dimethicone, PEG-9 polydimethylsiloxyethyl dimethicone, lauryl PEG-9 polydimethylsiloxyethyl dimethicone, and cetyl PEG/PPG-10/1 dimethicone. Examples of these commercially available products include KF-6011, KF-6043, KF-6017, KF-6017P, KF-6028, KF-6028P, KF-6038, and KF-6048 (all manufactured by Shin-Etsu Chemical Industry Co., Ltd.).

Examples of the silicone-based surfactant modified by a polyglycerin group include polyglyceryl-3 disiloxane dimethicone, polyglyceryl-3 polydimethylsiloxyethyl dimethicone, and lauryl polyglyceryl-3 polydimethylsiloxyethyl dimethicone. Examples of these commercially available products include KF-6100, KF-6104, KF-6106, and KF-6105 (all manufactured by Shin-Etsu Chemical Industry Co., Ltd.).

In addition to the silicone-based surfactant, for example, a surfactant such as polyglyceryl-2 diisostearate, and sorbitan sesquiisostearate can also be used.

The amount of the surfactant to be blended may be, from the viewpoint of emulsification stability and the like, 0.1% by mass or more, 0.5% by mass or more, or 1% by mass or more, and may be 8% by mass or less, 6% by mass or less, or 5% by mass or less, based on the total amount of the emulsified composition.

<Optional Ingredients>

In the water-in-oil emulsified composition of the present disclosure, various ingredients can be appropriately blended within a range that does not affect the effect of the present invention. Examples of the various ingredients include additive ingredients which can be usually blended into a cosmetic. Examples thereof include a moisturizing agent such as 1,3-butylene glycol, propylene glycol, and dynamite glycerin, a water-soluble polymer, a film-forming agent such as siliconized polysaccharides, a metal ion sequestering agent, a lower alcohol, a polyhydric alcohol such as PEG6000 and dipropylene glycol, various types of extracts, a sugar, an amino acid, an organic amine, a polymer emulsion, a chelating agent, an ultraviolet absorber, a pH adjusting agent, a skin nutritional agent, a vitamin, a water-soluble agent applicable to a medicine, a quasi-drug, and a cosmetic, an antioxidant, a buffering agent, a preservative, an antioxidant aid, a propellant, an organic-based powder, a clay mineral, a pigment, a dye, a coloring matter, a fragrance, water, acid components, alkali components and the like. These optional components may be used alone or in combination of two or more, and may be suitably blended in an oil phase or in an aqueous phase.

(Clay Mineral)

Among them, it is preferable to use a clay mineral from the viewpoint of emulsification stability under high temperature. Since the oil-soluble copolymer of the present disclosure is an organic substance, the thickening effect may decrease under high temperature, for example, in an environment of about 50° C. On the other hand, since the clay mineral is an inorganic substance, it is less susceptible to the effect under high temperature compared with an organic substance. Clay minerals have a lower thickening effect than the oil-soluble copolymers of the present disclosure, but have a performance of thickening the oil content. As a result, since the clay minerals can complement the thickening property due to the oil-soluble copolymer reduced under high temperature conditions, the use of clay minerals can improve the emulsification stability under high temperature.

There is no particular limitation on the clay mineral, and for example, a layered clay mineral such as bentonite, laponite, hectorite, montmorillonite, or magnesium aluminum silicate can be used alone or in combination of two or more. Such a clay mineral may be modified, for example, with a quaternary ammonium salt type cationic surfactant.

As the clay mineral, for example, a layered silicate mineral belonging to the genus smectide can be used, and a clay mineral such as colloidal hydrous aluminum silicate having a three layer structure represented by the following Formula 5 is preferred:

$$(X,Y)_{2-3}(Si,Al)_4O_{10}(OH)_2Z_{1/3} \cdot nH_2O \quad \text{Formula 5}$$

In Formula 5, X represents Al, Fe (III), Mn (III) or Cr (III), Y represents Mg, Fe (II), Ni, Zn, Li or Mn (II), and Z represents K, Na, ½Ca or ½Mg.

As a quaternary ammonium salt type cationic surfactant capable of modifying a clay mineral, for example, a compound represented by the following Formula 6 can be used:

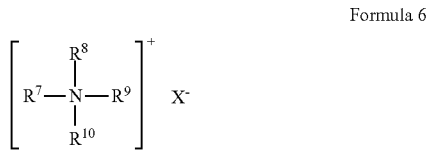

Formula 6

In Formula 6, $R^7$ represents an alkyl group having 10 to 22 carbon atoms or a benzyl group, $R^8$ represents a methyl group or an alkyl group having 10 to 22 carbon atoms, $R^9$ and $R^{10}$ each independently represents an alkyl group or a hydroxyalkyl group having 1 to 3 carbon atoms, and X represents a halogen atom or a methyl sulfate residue.

Such quaternary ammonium salt type cationic surfactants include, for example, dodecyltrimethylammonium chloride, myristyltrimethylammonium chloride, cetyltrimethylammonium chloride, stearyltrimethylammonium chloride, behenyltrimethylammonium chloride, myristyldimethylethylammonium chloride, cetyldimethylethylammonium chloride, stearyldimethylethyl ammonium chloride, behenyldimethylethylammonium chloride, myristyldiethylmethylammonium chloride, cetyldiethylmethylammonium chloride, stearyldiethylmethylammonium chloride, behenyldiethylmethylammonium chloride, benzyldimethylmyristylammonium chloride, benzyldimethylcetylammonium chloride, benzyldimethylstearylammonium chloride, benzyldimethylbehenylammonium chloride, benzylmethylethylcetylammonium chloride, benzylmethylethylstearylammonium chloride, distearyldimethylammonium chloride (distearyldimonium chloride), dibehenyldihydroxyethylammonium chloride, and compounds with bromide in place of chloride in each of the above compounds, and further, dipalmitylpropylethylammonium methylsulfate. Among them, benzyldimethylstearylammonium chloride and distearyldimethyl ammonium chloride are preferred.

Examples of the cationically modified clay mineral subjected to a modification treatment with a quaternary ammonium salt type cationic surfactant include dimethyldistearylammonium hectorite, dimethylalkylammonium hectorite, benzyldimethylstearylammonium hectorite, dimethyldistearyl ammonium bentonite, and magnesium aluminum silicate treated with distearyldimethylammonium chloride. Among them, magnesium aluminum silicate treated with distearyldimethylammonium chloride is preferable.

The blending amount of the clay mineral may be 0.10% by mass or more, 0.15% by mass or more, or 0.20% by mass or more, and may be 2.0% by mass or less, 1.5% by mass or less, or 1.0% by mass or less, based on the total amount of the water-in-oil emulsified composition.

<<Application of Water-In-Oil Emulsified Compositions>>

The water-in-oil emulsified composition of the present disclosure can be used, for example, as a base material of a cosmetic. The product form of such a cosmetic is not particularly limited, and examples thereof include skin care cosmetics such as emulsion, cream, face oil, body oil, and beauty liquid; makeup cosmetics such as foundation, cosmetic base, lipstick, blush, eye shadow, mascara, and mascara base; skin cleansers such as makeup dropping; hair cleansers; hair cosmetics such as hair treatment and hair oil; sunscreen cosmetics; hair dyes and the like.

<<Process for Producing Water-in-Oil Emulsion Compositions>>

The water-in-oil emulsified composition of the present disclosure can be produced using known methods. For example, an oil-soluble copolymer may be added to an oil content and stirred to prepare a mixed liquid, and water and a surfactant may be added to such a mixed liquid and stirred to obtain an emulsified composition of a water-in-oil type. If necessary, the above optional ingredients may be appropriately blended with respect to water or oil content.

EXAMPLES

Hereinafter, the present invention will be described in more detail with reference to Examples, but the present invention is not limited thereto. Note that, hereinafter, unless otherwise specified, the blending amount is indicated by mass %.

Examples 1 to 14 and Comparative Examples 1 to 4

<Synthesis of Oil-Soluble Copolymer 1>

To a 4 necked flask having a capacity of 1 liters to which a reflux condenser, a thermometer, a nitrogen gas introduction pipe and an agitator were attached, 250 parts by mass of ethanol, and 40 parts by mass of glyceryl methacrylate as a hydrophilic monomer, and 30 parts by mass of stearyl acrylate and 30 parts by mass of stearyl methacrylate as a hydrophobic monomer were charged, and the temperature was increased under a stream of nitrogen. At the time of reaching a reflux state of about 80° C., 1 parts by mass of 2,2'-azobisisobutyronitrile was added, and the polymerization reaction was allowed to proceed by maintaining a reflux state for 4 hours. Then, ethanol of the solvent was distilled off from the solution in the flask to obtain oil-soluble copolymer 1.

<Synthesis of Oil-Soluble Copolymer 2>

To a 4 necked flask having a capacity of 1 liters to which a reflux condenser, a thermometer, a nitrogen gas introduction pipe and an agitator were attached, 250 parts by mass of ethanol, 50 parts by mass of hydroxyethylacrylamide as a hydrophilic monomer, and 50 parts by mass of stearyl acrylate as a hydrophobic monomer were charged, and the temperature was raised under a nitrogen stream. At the time of reaching a reflux state of about 80° C., 1 parts by mass of 2,2'-azobisisobutyronitrile was added, and the polymerization reaction was allowed to proceed by maintaining a reflux state for 4 hours. Then, ethanol of the solvent was distilled off from the solution in the flask to obtain oil-soluble copolymer 2.

The composition obtained by the formulation and the manufacturing method of Table 1 and Table 2 shown below was evaluated for the average particle size and viscosity of water droplets in the composition immediately after preparation at room temperature (25° C.), and the average particle size and viscosity of water droplets after 4 weeks under each temperature. Incidentally, in Table 1 and Table 2, "after 4 weeks" is denoted as "4W".

<Evaluation Method>

(Evaluation of Average Particle Size)

Measurement of the average particle size of water droplets (emulsified particles) in the composition was observed by direct visual observation under an optical microscope (manufactured by BX60, OLYMPUS Co., Ltd.), and was determined as an average value of the projected area circle equivalent diameter of 10 water droplets arbitrarily selected. The results are summarized in Tables 1 and 2.

(Evaluation of Viscosity)

The viscosity of the composition was evaluated using a B-type viscometer (TVB-type viscometer TVB-10, manufactured by Toki Sangyo Co., Ltd.) under conditions of rotor number H6, 30° C., and 10 revolutions per minute. The results are summarized in Tables 1 and 2. Note that evaluation of the viscosity was not performed on the composition in the separated state.

Examples 1 to 3, Comparative Examples 1 to 3

In Examples 1 to 3 and Comparative Examples 1 to 3, the effect of the proportion of the polar oil occupying the oil content was evaluated.

Example 1

1.2 parts by mass of oil-soluble copolymer 1 and 2 parts by mass of cetyl PEG/PPG-10/1 dimethicone were added to 40 parts by mass of pentaerythrityl tetraethylhexanoate as an oil content, and the mixture was heated to 85° C., followed by stirring and dissolving to prepare mixed liquid A. 46.8 parts by mass of ion-exchanged water and 10 parts by mass of dynamite glycerin were heated and mixed at 80° C., thereby preparing mixed liquid B. A water-in-oil type emulsified composition was prepared by gradually adding and mixing mixed liquid B to mixed liquid A using a homogenizer, and then cooling to room temperature.

Examples 2 and 3, Comparative Examples 1 to 3

Examples 2 and 3 and Comparative Examples 1 to 3 were each prepared in the same manner as in Example 1, except that the blending ratio was changed to that of Table 1.

|  |  |  | Example 1 | Example 2 | Example 3 | Comparative Example 1 | Comparative Example 2 | Comparative Example 3 |
|---|---|---|---|---|---|---|---|---|
| Water | Ion-exchanged water |  | 46.8 | 46.8 | 46.8 | 46.8 | 46.8 | 46.8 |
| Moisturizing agent | Dynamite glycerin |  | 10 | 10 | 10 | 10 | 10 | 10 |
| Surfactant | Cetyl PEG/PPG-10/1 dimethicone |  | 2 | 2 | 2 | 2 | 2 | 2 |
| Oil content | Polar oil | Pentaerythrityl tetraethylhexanoate (IOB = 0.35) | 40 | 28 | 25 | 20 | 12 | — |
|  | Non-polar oil | Hydrogenated polydecene | — | 12 | 11 | 20 | 28 | 40 |
|  | Silicone oil | Dimethicone | — | — | 4 | — | — | — |
| Oil-soluble copolymer 1 |  |  | 1.2 | 1.2 | 1.2 | 1.2 | 1.2 | 1.2 |
| Total |  |  | 100 | 100 | 100 | 100 | 100 | 100 |
| The proportion of polar oil in oil content (mass %) |  |  | 100 | 70 | 62.5 | 50 | 30 | 0 |
| Immediately after preparation (25° C.) | Average particle size (μm) |  | 1 to 7.5 | 1 to 7.5 | 1 to 7.5 | 1 to 7.5 | 1 to 7.5 | 1 to 7.5 |
|  | Viscosity (mPa · s) |  | 39,200 | 19,800 | 23,400 | 12,700 | 9,600 | 2,900 |
| Average particle size (μm) | 0° C., 4W |  | 1 to 7.5 | 1 to 7.5 | 1 to 7.5 | 1 to 7.5 | 1 to 7.5 | 1 to 7.5 |
|  | 25° C., 4W |  | 1 to 7.5 | 1 to 7.5 | 1 to 7.5 | 1 to 7.5 | 1 to 7.5 | 1 to 10 |
|  | 37° C., 4W |  | 1 to 10 | 1 to 10 | 1 to 10 | Separation | Separation | Separation |
|  | 50° C., 4W |  | Separation | Separation | Separation | Separation | Separation | Separation |
| Viscosity (mPa · s) | 0° C., 4W |  | 32,500 | 13,250 | 14,200 | 8,900 | 6,900 | 2,450 |
|  | 25° C., 4W |  | 34,300 | 13,800 | 13,300 | 9,250 | 7,450 | 2,620 |
|  | 37° C., 4W |  | 29,800 | 12,500 | 12,600 | — | — | — |
|  | 50° C., 4W |  | — | — | — | — | — | — |

<Results>

As is apparent from Table 1, it could be confirmed that as the proportion of the polar oil occupied in the oil content increases, the viscosity of the composition also increases. It was also found that when the proportion of the polar oil in the oil content exceeds 50% by mass, the aqueous phase and the oil phase do not separate even after 4 weeks at 37° C., and the emulsification stability is excellent.

Examples 4 to 14 and Comparative Example 4

In Examples 4 to 14 and Comparative Example 4, the effect associated with the use of clay minerals was evaluated.

Example 4

0.6 parts by mass of oil-soluble copolymer 1, 0.2 parts by mass of distearyldimonium chloride as a modifier of clay minerals, 2 parts by mass of cetyl PEG/PPG-10/1 dimethicone, and 1 parts by mass of polyglyceryl-2 diisostearate were added to 12 parts by mass of pentaerythrityl tetraethylhexanoate, 12 parts by mass of cetyl ethylhexanoate, and 6 parts by mass of dimethicone as an oil content, and heated to 85° C. to stir and dissolve to prepare mixed liquid A. 5 parts by mass of dynamite glycerin and 5 parts by mass of dipropylene glycol were dissolved in 54.9 parts by mass of ion-exchanged water, and after heating to 80° C., 0.3 parts by mass of magnesium aluminum silicate as a clay mineral was added and stirred and dispersed to prepare mixed liquid B. A water-in-oil type emulsified composition was prepared by gradually adding and mixing mixed liquid B to mixed liquid A using a homogenizer, and then cooling to room temperature.

Examples 5 to 14

Each of the compositions of Examples 5 to 14 was prepared in the same manner as in Example 4, except that the blending ratio was changed to that of Table 2.

Comparative Example 4

A composition of Comparative Example 4 was prepared in the same manner as in Example 4, except that the blending ratio was changed to that of Table 2 and that an oil-soluble copolymer was not used. Note that, in the composition of Comparative Example 4, since the aqueous phase and the oil phase were separated after 4 weeks at 37° C., viscosity measurement after 4 weeks in an environment of 0° C. to 50° C. was not performed.

| | | Example 4 | Example 5 | Example 6 | Example 7 | Example 8 | Example 9 | Example 10 | Example 11 | Example 12 | Example 13 | Example 14 | Comparative Example 4 |
|---|---|---|---|---|---|---|---|---|---|---|---|---|---|
| Water | Ion-exchanged water | 54.9 | 54.7 | 44.8 | 44.5 | 44.7 | 44.7 | 44.7 | 44.7 | 44.7 | 44.7 | 44.7 | 45.5 |
| Moisturizing agent | Dynamite glycerin | 5 | 5 | 5 | 5 | 5 | 5 | 5 | 5 | 5 | 5 | 5 | 5 |
| | Dipropylene glycol | 5 | 5 | 5 | 5 | 5 | 5 | 5 | 5 | 5 | 5 | 5 | 5 |
| | PEG6000 | 1 | 1 | 1 | 1 | 1 | 1 | 1 | 1 | 1 | 1 | 1 | 1 |
| Surfactant | Cetyl PEG/PPG-10/1 dimethicone | 2 | 2 | 2 | 2 | 2 | 2 | 2 | 2 | 2 | 2 | 2 | 2 |
| | Polyglyceryl-2 diisostearate | 1 | 1 | 1 | 1 | 1 | 1 | 1 | 1 | 1 | 1 | 1 | 1 |
| Oil content | Polar oil | Pentaerythrityl tetraethylhexanoate (IOB = 0.35) | 12 | 15 | 18 | 18 | 25 | 25 | 15 | 10 | 11 | 11 | 18 | 18 |
| | | Diethylhexyl succinate (IOB = 0.32) | — | 6 | — | — | — | — | — | — | 13 | 16 | — | — |
| | | Cetyl ethylhexanoate (IOB = 0.13) | 12 | 6 | 18 | 18 | — | — | 22 | 27 | 13 | 10 | 18 | 18 |
| | Nonpolar oil | Hydrogenated polydecene | — | 3 | — | — | 11 | 11 | 3 | 3 | 3 | 3 | — | — |
| | Silicone oil | Dimethicone | 6 | — | 4 | 4 | 4 | 4 | — | — | — | — | 4 | 4 |
| Oil-soluble copolymer 1 | | 0.6 | 0.8 | 0.7 | 0.8 | 1 | 0.8 | 0.8 | 0.8 | 0.8 | 0.8 | — | — |
| Oil-soluble copolymer 2 | | — | — | — | — | — | — | — | — | — | — | 0.8 | — |
| Modifier | Distearyldimonium chloride | 0.2 | 0.2 | 0.2 | 0.2 | 0.2 | 0.2 | 0.2 | 0.2 | 0.2 | 0.2 | 0.2 | 0.2 |
| Clay mineral | Magnesium aluminum silicate | 0.3 | 0.3 | 0.3 | 0.3 | 0.3 | 0.3 | 0.3 | 0.3 | 0.3 | 0.3 | 0.3 | 0.3 |
| Total | | 100 | 100 | 100 | 100 | 100 | 100 | 100 | 100 | 100 | 100 | 100 | 100 |
| The proportion of polar oil in oil content (mass %) | | 80 | 90 | 90 | 90 | 62.5 | 62.5 | 92.5 | 92.5 | 92.5 | 92.5 | 90 | 90 |
| Immediately after preparation | Average particle size (μm) | 1 to 5 | 1 to 5 | 1 to 5 | 1 to 5 | 1 to 5 | 1 to 5 | 1 to 5 | 1 to 5 | 1 to 5 | 1 to 5 | 1 to 5 | 1 to 7.5 |
| | Viscosity (mPa·s) | 11,600 | 45,600 | 9,000 | 10,000 | 20,000 | 16,200 | 5,800 | 4,000 | 7,330 | 8,510 | 12,300 | 1,660 |
| Average particle size (μm) | 0° C., 4W | 1 to 5 | 1 to 2.5 | 1 to 5 | 1 to 5 | 1 to 5 | 1 to 5 | 1 to 5 | 1 to 5 | 1 to 5 | 1 to 5 | 1 to 5 | 1 to 10 |
| | 25° C., 4W | 1 to 5 | 1 to 2.5 | 1 to 5 | 1 to 5 | 1 to 5 | 1 to 5 | 1 to 5 | 1 to 5 | 1 to 5 | 1 to 5 | 1 to 5 | 1 to 10 |
| | 37° C., 4W | 1 to 5 | 1 to 2.5 | 1 to 5 | 1 to 5 | 1 to 5 | 1 to 5 | 1 to 5 | 1 to 5 | 1 to 5 | 1 to 5 | 1 to 5 | Separation |
| | 50° C., 4W | 1 to 10 | 1 to 2.5 | 1 to 5 | 1 to 5 | 1 to 5 | 1 to 5 | 1 to 5 | 1 to 5 | 1 to 5 | 1 to 5 | 1 to 7.5 | Separation |
| Viscosity (mPa·s) | 0° C., 4W | 18,100 | 33,100 | 8,400 | 11,700 | 17,500 | 16,400 | 6,920 | 4,520 | 5,540 | 6,040 | 14,800 | — |
| | 25° C., 4W | 18,000 | 41,700 | 14,700 | 16,100 | 19,600 | 19,200 | 8,260 | 6,330 | 6,690 | 7,330 | 14,900 | — |
| | 37° C., 4W | 16,000 | 35,500 | 9,200 | 9,700 | 14,600 | 16,700 | 5,850 | 4,740 | 5,680 | 6,840 | 12,000 | — |
| | 50° C., 4W | 15,000 | 24,500 | 7,400 | 7,900 | 17,100 | 15,400 | 5,880 | 4,970 | 6,010 | 7,810 | 6,600 | — |

\<Results\>

As is apparent from Table 2, in the composition of Comparative Example 4 containing a clay mineral but not containing an oil-soluble copolymer, the aqueous phase and the oil phase were separated after 4 weeks at 37° C. On the other hand, the compositions of Examples 4 to 14 containing the oil-soluble copolymer and the clay mineral were not separated from the aqueous phase and the oil phase even after 4 weeks at 37° C. and after 4 weeks at 50° C., and were found to be excellent in emulsification stability under high temperature.

\<\<Example of Cosmetic Formulation\>\>

Hereinafter, an example of formulation when the water-in-oil emulsified composition of the present disclosure is used as a cosmetic will be described, but the present invention is not limited to this illustration.

Formulation Example: Sunscreen Cosmetic

| (Ingredients) | (% by mass) |
| --- | --- |
| Ion exchange water | remainder |
| Dynamite glycerin | 5 |
| Dipropylene glycol | 5 |
| PEG600 | 1 |
| Cetyl PEG/PPG-10/1 dimethicone | 2 |
| Polyglyceryl-2 diisostearate | 1 |
| Pentaerythrityl tetraethylhexanoate | 12 |
| Cetyl ethylhexanoate | 12 |
| Polybutylene glycol | 2 |
| Octyl methoxycinnamate | 3 |
| Octocrylene | 5 |
| Bisethylhexyloxyphenol methoxyphenyl triazine | 1.5 |
| Hexyl diethylaminohydroxybenzoylbenzoate | 2 |
| Tert-butylmethoxydibenzoylmethane | 2.5 |
| Oil-soluble copolymer 1 | 0.8 |
| Distearyldimonium chloride | 0.2 |
| Magnesium aluminum silicate | 0.3 |

(Method for Producing a Sunscreen Cosmetic)

To an oil content containing pentaerythrityl tetraethylhexanoate, cetyl ethylhexanoate and polybutylene glycol, cetyl PEG/PPG-10/1 dimethicone, polyglyceryl-2 diisostearate, oil-soluble copolymer 1, distearyldimonium chloride which is a modifier of a clay mineral, octyl methoxycinnamate, octocrylene, bisethylhexyloxyphenol methoxyphenyltriazine, hexyl diethylaminohydroxybenzoylbenzoate and t-butylmethoxydibenzoylmethane were added, and the mixture was stirred and dissolved at 85° C., thereby preparing mixed liquid A. Dynamite glycerin, dipropylene glycol, and PEG6000 were dissolved in ion-exchanged water, and after heating to 80° C., magnesium aluminum silicate as a clay mineral was added and stirred and dispersed to prepare mixed liquid B. A water-in-oil type sunscreen cosmetic was prepared by gradually adding and mixing mixed liquid B to mixed liquid A using a homogenizer, and then cooling to room temperature.

REFERENCE SIGNS LIST

1 Water-in-oil emulsified composition
2 Oil-soluble copolymer
3 Hydrogen bond

The invention claimed is:

1. A water-in-oil emulsified composition comprising,
a dispersion medium comprising an oil content, and an oil-soluble copolymer having a monomer unit obtained from at least one hydrophilic monomer selected from Formula 1 and Formula 2 below, and a monomer unit obtained from a hydrophobic monomer of Formula 4 below; and
water droplets dispersed in the dispersion medium,
wherein the oil content contains 60% by mass or more of polar oil with an IOB of 0.10 or more, and
wherein the water droplets contain water and a surfactant, and the content of the water is 30% by mass or more based on the total amount of the composition:

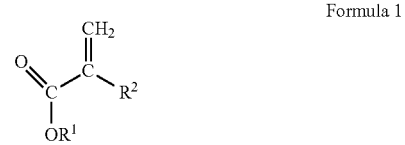

Formula 1 wherein,
$R^1$ is a hydrogen atom, a glyceryl group, a linear or branched hydroxyalkyl group having 1 to 4 carbon atoms, or a polypropylene glycol group indicated by $-(C_3H_6O)_nH$ and where n is an integer of 2 to 10, and
$R^2$ is a hydrogen atom or a methyl group,

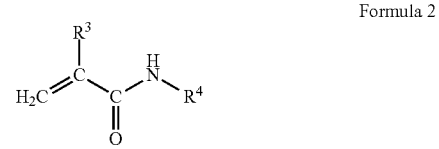

Formula 2 wherein,
$R^3$ is a hydrogen-atom or a methyl-group, and
$R^4$ is a linear or branched alkyl or hydroxyalkyl group having 1 to 4 carbon atoms, or a substituent of Formula 3 below,

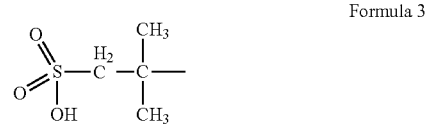

Formula 3

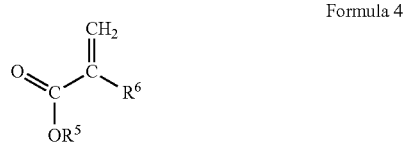

Formula 4 wherein,
$R^5$ is a linear or branched alkyl group having 16 to 22 carbon atoms, and
$R^6$ is a hydrogen atom or a methyl group.

2. The composition of claim 1, wherein the monomer of formula 1 is selected from at least one of 2-hydroxyethyl (meth)acrylate, glyceryl (meth)acrylate, PPG-6 (meth)acrylate, 2-hydroxypropyl (meth)acrylate, 2-hydroxy-2-methylpropyl (meth)acrylate, and (meth)acrylic acid, and wherein the monomer of formula 2 is selected from at least one of N-(2-hydroxyethyl) (meth)acrylamide, N-isopropyl (meth)acrylamide, and 2-(meth)acrylamide-2-methylpropanesulfonic acid.

3. The composition according to claim 1, wherein the monomer of Formula 4 is selected from at least one of cetyl (meth)acrylate, stearyl (meth)acrylate, isostearyl (meth) acrylate, and behenyl (meth)acrylate.

4. A composition according to claim 1, wherein in the oil-soluble copolymer, a monomer unit of the hydrophilic monomer is contained in a range of 30 to 50 mol %, and a monomer unit of the hydrophobic monomer is contained in a range of 50 to 70 mol %.

5. A composition according to claim 1, wherein the water droplet has an average particle size of 10 μm or less.

6. A composition according to claim 1, further comprising a clay mineral.

7. A cosmetic base material comprising a composition according to claim 1.

* * * * *